United States Patent [19]

Dell et al.

[11] Patent Number: 4,584,192

[45] Date of Patent: Apr. 22, 1986

[54] FILM-FORMING COMPOSITION CONTAINING AN ANTIMICROBIAL AGENT AND METHODS OF USE

[75] Inventors: John D. Dell, St. Paul; Milton H. Andrus, Jr., White Bear Lake, both of Minn.

[73] Assignee: Minnesota Mining & Manufacturing Company, St. Paul, Minn.

[21] Appl. No.: 617,255

[22] Filed: Jun. 4, 1984

[51] Int. Cl.$^4$ .............................................. A61F 31/78
[52] U.S. Cl. ..................................... 424/81; 424/150; 514/635
[58] Field of Search .................................. 424/81, 180

[56] References Cited

U.S. PATENT DOCUMENTS

| | | | |
|---|---|---|---|
| 2,804,073 | 8/1957 | Gallienne et al. | 128/156 |
| 3,216,579 | 11/1965 | Shelanski et al. | 424/80 X |
| 3,216,983 | 11/1965 | Shelanski et al. | 260/88.3 |
| 3,577,516 | 5/1971 | Gould et al. | 424/46 |
| 3,608,070 | 9/1971 | Nouvel | 424/80 |
| 3,621,079 | 11/1971 | Leeds | 424/80 X |
| 3,671,545 | 6/1972 | Halpern | 424/80 X |
| 3,907,720 | 9/1975 | Field et al. | 424/78 X |
| 3,928,556 | 12/1975 | Sweger | 424/45 |
| 3,932,602 | 1/1976 | Sweger | 424/45 |
| 3,975,350 | 8/1976 | Hudgin et al. | 260/30.4 |
| 4,310,509 | 1/1982 | Berglund et al. | 424/28 |
| 4,323,557 | 4/1982 | Rosso et al. | 424/28 |
| 4,374,126 | 2/1983 | Cardarelli et al. | 424/81 |

FOREIGN PATENT DOCUMENTS 2557607 7/1976 Fed. Rep. of Germany.
2924042 10/1980 Fed. Rep. of Germany.

*Primary Examiner*—Leonard Schenkman
*Attorney, Agent, or Firm*—Donald M. Sell; James A. Smith; Robert W. Sprague

[57] ABSTRACT

A film-forming composition containing a broad spectrum antimicrobial as an antimicrobial agent. The composition forms a film which is a substantially fluid-resistant, substantially tack-free, flexible film which adheres to skin and releases the antimicrobial agent to skin. A method of using the film-forming composition is also disclosed.

26 Claims, No Drawings

FILM-FORMING COMPOSITION CONTAINING AN ANTIMICROBIAL AGENT AND METHODS OF USE

This invention relates to a dermatologically acceptable, film-forming composition containing an antimicrobial agent. More specifically, it relates to film-forming compositions useful in promoting asepsis on skin. Methods of using the composition are also within the scope of the invention.

In order to control infection and promote healing in patients having surgical incisions or other open wounds, it has become standard hospital practice to apply an antimicrobial agent to the wound. The application of antimicrobial agents is also practiced during surgical operations to promote asepsis on skin adjacent to the incision site. Surgical incise drapes are also often employed in surgical operations to further promote asepsis in the operating field.

Topical application of antimicrobial agents has been accomplished using, for example, preoperative skin preps, surgical scrub tissues, washes, wound cleaners, lotions and ointments. Since microorganisms may survive the initial application of the antimicrobial agent, it is often necessary to reapply the agent in order to provide continued asepsis. Also, since antimicrobial agents are often water-soluble and are, therefore, subject to removal from the wound site when the site is sponged, irrigated or the like, reapplication of the antimicrobial agent may be necessary to assure continued asepsis.

Topical application of antimicrobial agents has also been accomplished using surgical incise drapes which comprise an antimicrobial agent-containing pressure-sensitive adhesive layer. For example, U.S. Pat. Nos. 4,310,509 (Berglund et al.) and 4,323,557 (Rosso et al.) describe surgical incise drapes which comprise such an adhesive and provide continued asepsis. More specifically, the Berglund patent describes a pressure-sensitive adhesive composition which contains chlorhexidine or a complex of polyvinylpyrrolidone and iodine, chlorhexidine and iodine being particularly effective antimicrobial agents. The Rosso patent describes a pressure-sensitive adhesive comprising N-vinylpyrrolidone residues in the polymer backbone. Iodine is complexed with these residues.

Further, topical application of antimicrobial agents has been accomplished using film-forming compositions which are applied to skin as liquids and contain amtimicrobial agents, e.g., see U.S. Pat. Nos. 2,804,073 (Gallienne et al.), 3,577,516 (Gould et al.), 3,608,070 (Nouvel) and 3,975,350 (Hudgin et al.).

Film-forming compositions comprising iodine in the form of a complex with a N-vinylpyrrolidone-residue-containing polymer are also known to the art, e.g., see U. S. Pat. 3,216,983 (Shelanski et al.) and West German Offenlegungsschrift No. 25 57 607 (laid-open July 8, 1976). The Shelanski patent discloses what are described as relatively water-insoluble films obtained by reacting polyvinylpyrrolidone or a polyvinylpyrrolidone/vinyl acetate copolymer with a diisocyanate. Iodine is complexed with the polyvinylpyrrolidone units contained in the resulting polymer.

The West German Offenlegungsschrift discloses what is described as a water-insoluble complex of iodine with an acrylic polymer containing N-vinylpyrrolidone residues. Water-insolubility of the complex is achieved by employing a relatively large amount of iodine which is complexed through incorporation of N-vinylpyrrolidone in the acrylic polymer in a relatively high level (i.e., at least 20% by weight based upon the total weight of all monomers in the polymer). While N-vinylpyrrolidone itself is hydrophilic and would increase water solubility, it is necessarily employed in a large amount in order to complex the large amount of iodine being employed. Otherwise, in the absence of a high level of N-vinylpyrrolidone, the composition would be expected to release iodine uncontrollably to skin and would therefore be dermatologically-unacceptable.

The prior art has not provided a film-forming composition which is totally acceptable from the standpoint of convenience, comfort, safety and efficacy in promoting asepsis on skin. A good film-forming composition should be dermatologically-acceptable and capable of application to skin conveniently as a solution in a dermatologically-acceptable solvent which evaporates quickly on skin. The film resulting from application of such a solution should be fluid-resistant and non-tacky, and should permit facile transmission of water vapor therethrough. The film should be clear, to permit, for example, viewing of the site where an incision will be made during a surgical procedure. It should further adhere suitably to skin and be capable of releasing the antimicrobial agent onto the skin over a period of time to promote asepsis for a suitably long period of time. Additionally, the resulting film should exhibit skin-like physical properties such as a degree of flexibility so that the film will retain its integrity during wound retraction, etc.. The film should be soluble in a dermatologically acceptable solvent such as a lower alkyl alcohol which may be used as or in a remover solution which is employed to remove the film once the surgical procedure has been completed.

The film-forming composition of the present invention successfully meets the aforementioned criteria.

BRIEF SUMMARY OF THE INVENTION

The present invention provides a film-forming composition comprising:
(a) a film-forming copolymer consisting essentially of copolymerized A, B and C monomers as follows:
A is a monomeric acrylic or methacrylic acid ester of an alkyl alcohol containing a single hydroxyl, the alcohol being further described as having from 2 to about 14 carbon atoms when the A monomer is an acrylic acid ester, and about 7 to 18 carbon atoms when the A monomer is a methacrylic acid ester, the amount by weight of A monomer being about 15 to 80% of the total weight of all monomers in the copolymer;
B is a monomeric methacrylic acid ester of an alkyl alcohol containing a single hydroxyl, the alcohol being further described as having from 1 to about 6 carbon atoms, the amount by weight of B monomer being about 20 to 70% of the total weight of all monomers in the copolymer; and
C is an N-vinyl lactam, the amount by weight of which being about 1 to 15% of the total weight of all monomers in the copolymer;
(b) an effective amount of a broad spectrum antimicrobial agent;
the composition being dermatologically-acceptable, and, when applied to skin from a fugitive solvent, being capable of forming a clear, substantially fluid-resistant, substantially tack-free, flexible film which adheres to skin and releases the antimicrobial agent to skin.

A preferred film-forming composition of the invention comprises iodine as the antimicrobial agent, the iodine forming a complex with the film-forming copolymer via the N-vinyl lactam residues contained therein, and being present in an amount by weight of about 0.1 to 15% of the total weight of the film-forming copolymer and the iodine.

The method of using the composition of the present invention to cover skin with a film exhibiting antimicrobial activity and to thereby promote asepsis comprises the steps of:
(a) applying the composition to the skin;
(b) allowing the composition to dry to form a film; and
(c) allowing said film to remain on the skin to promote asepsis.

The present invention solves the problems associated with prior art compositions by providing a film-forming composition which exhibits the following characteristics. The film-forming composition is dermatologically-acceptable and may be applied to skin conveniently as a solution in a dermatologically-acceptable, volatile solvent such as ethanol or isopropanol. Due to the nature of the film-forming polymer, the composition of the invention does not require the presence of a fugitive plasticizer. The film resulting from the application of the composition is bacteria-impermeable and substantially fluid-resistant and non-tacky, and permits facile transmission of moisture vapor therethrough. Further, the film is clear and therefore allows viewing of the underlying skin. Also, the film adheres suitably to skin and releases the antimicrobial agent contained therein to skin upon contact of the film with skin. The film is soluble in dermatologically-acceptable lower alkyl alcohols such that it may be removed conveniently using a remover solution comprising such an alcohol. Since the film-forming composition of the invention is applied to skin from solutions, complete conformability of the resulting film to the contours of the patient is assured. The composition of the invention is particularly suitable for use as pre-surgical skin preparations. The composition is also particularly suitable for promoting asepsis in and around puncture wounds such as sites of injection or catheterization.

The compositions of the invention may also be used in liquid bandages, coating for percutaneous access device sites, stoma seals, various general hospital uses, teat dips, and liquid gloves for medical use or food-handling, and the like.

The desirable balance of properties exhibited by the film-forming composition of the invention results from the incorporation into the film-forming copolymer of particular types of monomers and amounts thereof. As noted above, the film-forming copolymer consists essentially of A, B and C monomers. The A monomer is believed to provide flexibility and elongation, and also results in a copolymer which exhibits the desired adhesiveness to skin. Further, the A monomer provides a degree of hydrophobicity which results in the desired fluid-resistance to bodily fluids and the like. The B monomer provides strength and tensile and also results in a copolymer which is non-tacky. Finally, the C monomer permits transmission of moisture vapor through the resulting film, and further provides sites for the complexation of iodine (when iodine is the antimicrobial agent) so as to provide a dermatologically-acceptable composition. It is only through proper selection of monomers and amounts thereof that a film-forming composition exhibiting the desired properties is obtained.

DETAILED DESCRIPTION OF THE INVENTION

The composition of the present invention is dermatologically-acceptable and provides a film which is clear and substantially fluid-resistant. As used in the instant specification and claims, the term "dermatologically-acceptable" means that the composition does not cause either substantial irritation to skin or patient sensitization as the result of contact therewith. As used in the instant specification and claims the term "clear" means that a film provided by the compositions of the invention is transparent and free of turbidity. As used in the instant specification and claims, the phrase "substantially fluid-resistant" means that a film retains its integrity when contacted with bodily fluids (e.g., blood and perspiration), irrigation fluids and the like even when the film is rubbed lightly.

As indicated above, the A monomer of the film-forming copolymer is a monomeric acrylic or methacrylic acid ester of an alkyl alcohol containing a single hydroxyl. When the A monomer is an acrylic acid ester, the alcohol contains from 2 to about 14 carbon atoms, and preferably about 4 to 14 carbon atoms. When the A monomer is a methacrylic acid ester, the alcohol contains about 7 to 18 carbon atoms, and preferably about 10 to 18 carbon atoms. As noted above, presence of the A monomer in the film-forming copolymer provides flexibility and elongation and the desired level of adhesiveness to skin. The A monomer further provides a degree of hydrophobicity which results in the desired resistance to blood.

Examples of suitable acrylic acid esters for use as the A monomer include the esters of acrylic acid with non-tertiary alcohols such as ethanol, 1-butanol, 2-butanol, 1-pentanol, 2-pentanol, 3-pentanol, 2-methyl-1-butanol, 1-hexanol, 2-hexanol, 2-methyl-1-pentanol, 3-methyl-1-pentanol, 2-ethyl-1-butanol, 3,5,5-trimethyl-1-hexanol, 3-heptanol, 1-octanol, 2-octanol, isooctyl alcohol, 2-ethyl-1-hexanol, 1-decanol, 1-dodecanol, 1-trideconol, 1-tetradecanol and the like.

Examples of suitable methacrylic acid esters for use as the A monomer include the esters of methacrylic acid with non-tertiary alcohol such as 3-heptanol, 1-octanol, 2-octanol, isooctyl alcohol, 2-ethyl-1-hexanol, 1-decanol, 1-dodecanol, 1-tridecanol, 1-tetradecanol, 1-octadecanol and the like.

The preferred A monomer is selected from the group consisting of n-butyl acrylate, isooctyl acrylate and lauryl methylacrylate (the methacrylic acid ester of 1-dodecanol).

It is to be understood that the film-forming copolymer may comprise a single type of A monomer or may comprise two or more different A monomers.

Monomer B of the film-forming copolymer is a monomeric methacrylic acid ester of an alkyl alcohol containing a single hydroxyl. The alcohol contains from 1 to about 6 carbon atoms, and preferably 1 to about 4 carbon atoms. Again as noted above, presence of the B monomer in the film-forming copolymer provides strength and tensile and also results in a copolymer which is non-tacky.

Examples of suitable monomers for use as the B monomer include the esters of methacrylic acid with non-tertiary alcohols such as methanol, ethanol, 1-propanol, 2-propanol, 1-butanol, 2-butanol, 1-pentanol, 2-pentanol and 3-pentanol.

The preferred B monomer is selected from the group consisting of methyl methacrylate and n-butyl methacrylate.

It is to be understood that the film-forming copolymer may comprise a single type of B monomer or may comprise two or more different B monomers.

The C monomer is an N-vinyl lactam which is capable of complexing iodine. Examples of suitable N-vinyl lactams which may be employed include those disclosed in U.S. Pat. No. 3,907,720 (Field et al) incorporated herein by reference. That patent discloses, for example, N-vinyl-substituted derivatives of the following lactams: 3,3-dimethyl-1-pyrrolidone, 4,4-dimethyl-2-pyrrolidone, 3,4-dimethyl-2-pyrrolidone, 3-ethyl-2-pyrrolidone, and 3,5-dimethyl-2-pyrrolidone. The preferred N-vinyl lactam is N-vinylpyrrolidone.

It is to be understood that the film-forming copolymer may comprise a single type of C monomer or may comprise two or more different C monomers.

The properties of the film-forming copolymer vary depending on the particular combination and relative amounts of the A, B and C monomers employed in preparing the copolymer. The combination of types and amounts of A, B and C monomers is such that the resulting film-forming composition is dermatologically-acceptable, and when applied to skin from a fugitive solvent, is capable of forming a substantially fluid-resistant, substantially tack-free, flexible film which adheres to skin and releases the antimicrobial agent to skin. Thus, any combination of types of A, B and C monomers may be employed so long as the resulting copolymer exhibits the required properties.

As to amounts of the respective monomers, the A monomer is present in an amount of about 15 to 80% of the total weight of all monomers in the copolymer, the B monomer is present in an amount of about 20 to 70% of the total weight of all monomers, and the C monomer is present in an amount of about 1 to 15% of the total weight of all monomers. The particular amounts of the A, B and C monomers employed depends on the nature of the A, B and C monomers selected. The amounts of the various monomers may be varied within the above ranges so long as the resulting film-forming composition exhibits the indicated properties. Preferred amounts for the A, B and C monomers are about 40 to 60%, 25 to 50% and 5 to 15%, respectively, based upon the total amount of all monomers in the copolymer.

Copolymers containing solely A, B and C monomers of appropriate types and appropriate amounts perform suitably in the practice of the invention. However, the copolymers of the invention may further include minor amounts of non-essential monomers such as styrene, butadiene and/or isoprene. The copolymers, however, are free of substantial amounts of acid functional monomers, since inclusion of such adversely affects fluid-resistant of the resulting film-forming composition.

The film-forming copolymers may be prepared using conventional free-radical-polymerization methods. One particularly convenient method is the following: The desired amounts of A, B and C monomers and an organic solvent in which the monomers are soluble are combined in a sealable bottle. A particularly suitable solvent is acetone. A catalytic amount of a free-radical-initiator such as $\alpha,\alpha'$-azobisisobutyronitrile is then added to the solution. Nitrogen is passed through the air space above the solution to purge air from within the bottle and the bottle is then sealed. The sealed bottle is tumbled in a heated water bath for a period of time sufficient to effect essentially complete polymerization. Generally, 24 hours has been found to be sufficient time to effect essentially complete polymerization when the water bath is maintained at about 55° C.

The antimicrobial agent which is included in the compositions of the present invention may be any broad spectrum antimicrobial agent which is suitable for topical application. An example of a suitable antimicrobial agent is chlorhexidine or a suitable derivative thereof such as chlorhexidine gluconate or chlorhexidine acetate. The antimicrobial agent is present in these compositions in an effective amount (i.e., an amount which provides for release of the antimicrobial agent from the film substantially continuously over a sustained period of time such as about 30 minutes). For example, when the antimicrobial agent is chlorhexidine or a derivative thereof, the film-forming composition will preferably contain the antimicrobial agent in an amount by weight of about 4 to 10% based on the total weight of the film-forming copolymer and the antimicrobial.

The preferred antimicrobial agent for inclusion in the compositions of the invention is iodine. It is believed that iodine forms a complex with the N-vinyl lactam residues in the film-forming copolymer and that iodine release from the films obtained from the compositions of the present invention is a function of the level of such N-vinyl lactam residues in the film-forming copolymer.

As a general statement, film-forming compositions comprising about 0.1 to 15% iodine based on the total weight of the film-forming copolymer and iodine provide films exhibiting suitable antimicrobial activity. Preferred film-forming compositions are those containing iodine in an amount by weight of about 2 to 12% of the total weight of the film-forming copolymer and iodine. The most preferred composition contains iodine in an amount by weight of 5% based on the total weight of the film-forming copolymer and iodine. Again, as indicated above, the actual amount of iodine employed will depend in part on the amount of N-vinyl lactam residue contained in the copolymer. While not wishing to be bound to any particular theory, it is believed that, in order to insure that iodine will be released from the film-forming composition on contact with skin, the amount of N-vinyl lactam residue in the copolymer should generally be decreased with decreasing amounts of iodine employed.

It is preferred that iodine be added to the film-forming polymer as a solution in a solvent such as ethanol. The solution desirably also contains inorganic iodide (e.g., sodium or potassium iodide). While not wishing to be bound to any particular theory, it is believed that iodide ion increases the stability of the complex involving iodine and an N-vinylpyrrolidone residue. A suitable iodine-containing solution comprises a 0.5:1 to 4:1 molar ratio of iodide-iodine. The preferred molar ratio is 2:1 iodide:iodine.

The composition of the invention may further include conventional additives such as plasticizers, colorants, tackifiers and/or stabilizers to achieve desired properties. Selection of such additives and amounts thereof is within the ambit of the ordinary skill in the art.

The composition of the present invention is preferably applied to skin as a solution in a fugitive solvent which evaporates at a suitable rate when the composition is in contact with skin. Examples of suitable solvents which solubilize the film-forming copolymer and exhibit suitable volitility are ethanol and isopropanol. Acetone may also be used, but is less preferred. Preferably, the film-forming composition will comprise a fugitive solvent in an amount of about 20 to 1000 parts by weight per 10 parts by weight of the total of the film-forming copolymer and the antimicrobial agent (e.g., iodine), and more preferably will comprise about 40–190 parts by weight per 10 parts by weight of the total of the film-forming copolymer and the antimicrobial agent. The most preferred composition comprises 90 parts by weight of solvent per 10 parts by weight of the total of the film-forming copolymer and the antimicrobial agent. A sponge or gauze is the preferred means by which to apply the film-forming composition to skin.

Alternatively, the film-forming compositions of the invention may be applied to skin as an areosol.

Preferably, the film-forming composition is applied to skin in a thickness which provides a film which, when dry, is about 0.1 to 1 mil in thickness.

Films formed from a film-forming composition of the invention may be removed conveniently using a remover solution such as isopropanol. Alternatively, when the film is covered during a surgical procedure with a surgical drape which includes a pressure-sensitive adhesive layer, the film may conveniently be removed by removing the surgical drape (due to contact of the film with the adhesive layer of the surgical drape).

In some instances, it may be desirable to simply allow the film to wear-off with time as opposed to removing it, for example, with a remover solution as described above.

The compositions of the invention desirably can be exposed to a dose of 2.5 megarads of gamma irradiation without substantial alternation of the physical appearance or physical properties such as nontackiness and fluid-resistance. Such irradiated compositions will further desirably retain suitable antimicrobial activity.

The invention is further illustrated by the following non-limiting examples.

TEST METHOD A—SURFACE TACK

A method for determining whether a composition provides a film which exhibits substantially no tack is the following.

A composition is coated onto Scotchpar ® brand polyester film (commercially available from 3M) using a #26 wirewound coating rod (commercially available from R. D. Specialities, Webster, N.Y.). The coating is allowed to dry for 15 minutes under conditions of 22° C. and 45% Relative Humidity. A 2-inch by 2-inch (5.08 cm by 5.08 cm) piece of Red Cross Cotton (long fiber virgin purified cotton USP) which is commercially available from Johnson and Johnson Company, is placed on the coating and is overlayed with a 102 g, flat-bottomed circular weight having a surface area of 2.75 inches$^2$ (17.7 cm$^2$). After 60 seconds, the weight and cotton batting are removed and the coating is examined with the naked eye for the presence of fibers of cotton adhered thereto. A film which dries suitably to a substantally non-tacky state will have essentially no visible fibers adhered thereto.

TEST METHOD B—BLOOD RESISTANCE

One method for determining the degree of fluid-resistance exhibited by a composition is the following:

Substrates are prepared as follows: Full thickness sections of the lateral aspect of the thoracic and abdominal area (approximately 8 inches by 12 inches or 20.3 cm by 30.5 cm) of clipped and shaved pig skin are removed from a recently sacrificed pig. The pig skin sections are placed in polyethylene bags, sealed with a twist-tie, and refrigerated. It if is desired to store the pig sections for a period of time longer than a week, the sections should be covered with saline solution and frozen.

At the time of testing, the pig skin is allowed to warm to room temperature and is mounted on a board under light tension. The surface is washed with 2-propanol and wiped dry with a piece of clean gauze.

The film-forming composition which, for purposes of this test only, has had solvent added thereto or removed therefrom as necessary to provide a composition which is 10% solids by weight, is applied using a piece of polyurethane sponge to a section of pig skin which has been cleaned, dried and equilibrated to room temperature as described above. The composition should cover an area approximately 2 inches by 6 inches (5.08 cm by 15.2 cm) in dimension. The composition should be applied to pig skin in a manner such that if applied to a synthetic film backing (e.g. a polyester backing) in a similar manner, a uniform film which is in the range of about 0.3–0.4 mil in thickness (when dry) would be obtained.

After allowing the composition (which has been applied to the pig skin) to dry for 10 minutes, a gauze strip which is 1.5 inches by 7 inches (3.8 cm by 17.8 cm) and has been soaked with heparinized pig blood is placed perpendicular to the strip of the film formed by the film-forming composition. Care is taken to insure good contact between the soaked gauze and film surface. Since the soak time is 90 minutes, the gauze is re-wetted with heparinized pig blood (using a syringe) at 10–15 minute intervals or as needed to maintain the gauze saturated.

The gauze strip is removed at 90 minutes. After removal, the area is gently rinsed with tap water from a wash bottle. The area is blotted dry and inspected for appearance change (loss of color, change of color, loss of polymer, etc).

The test area is then scrubbed using light finger pressure with a saline-soaked gauze until the polymer looses adhesion and is rubbed away from the pig skin surface. The number of scrubs to achieve failure are recorded.

Each composition is tested on three different sections of pig skin with five independent tests being run for each composition on each section of pig skin. The average number of scrubs to achieve failure is then calculated.

Preferred film-forming compositions of the present invention, when tested as described above, will provide films which show essentially no appearance change after an average of at least about 20 scrubs.

In order to facilitate the visual observations required under this test method, it may be desirable to include a dye in those film-forming compositions which are colorless due to, for example, the presence therein of a colorless antimicrobial agent rather than iodine. As the dye functions only to aid visualization of appearance changes in the film, it should be present in a small amount only.

TEST METHOD C—ADHESION TO SKIN

A method for determining whether a composition provides a film which exhibits suitable adhesion to skin is the following.

Pig skin obtained as described in Test Method B is cleaned with isopropyl alcohol and cotton gauze, and is allowed to dry. A film-forming composition is applied to the skin by wiping on a thin, uniform film. When the film formed by the composition is completely dry, a 1-inch by 4-inch (1.54 cm by 10.2 cm) piece of the pressure-sensitive drape which is available under the trade designation Steri-Drape ® 2 from 3M is placed over the composition. Good contact is insured by rolling the tape piece twice with a 5 lb. (2.3 kg) rubber roller. The drape strip is loosened at one end and clamped into a 1-inch (2.54 cm) wide jaw of a device that pulls the film at a constant rate of 19 inches per minute (48.3 cm per minute) and measures via a transducer the peel force that results. The angle of the peel is about 180° and the peel force measured is expressed in grams/inch width. A suitable composition is one which forms a film exhibiting a peel adhesion of at least about 50 grams per inch width (19.7 g per cm).

TEST METHOD D—TENSILE AND ELONGATION

Tensile strength and elongation are determined in accordance with the ASTM test which is entitled "Standard Test Method For Tensile Properties of Plastics" and designated ASTM-D-882-81, incorporated herein by reference. The composition to be tested contains only the particular film-forming copolymer together with a suitable solvent for casting a film. That composition is coated onto release paper (e.g., Polyslik ® S-8004 from H. P. Smith Co.) to provide a film having a thickness of about 1.5 mil (0.0038 centimeters) when dry. The jaw separation rate to be employed in the testing procedure is 20 inches (50.8 cm) per minute.

Preferred copolymers of the invention exhibit a tensile strength of at least about 500 psi, and an elongation value of between about 100% and 1000%. Copolymers exhibiting a tensile strength of less than about 500 psi and an elongation of greater than about 100% generally will exhibit substantial tack. Tensile strength and particularly elongation are useful measurements for characterizing, in part, the relative degree of flexibility of a film.

EXAMPLE 1

A film-forming composition of the invention was prepared as follows.

A film-forming copolymer containing isooctyl acrylate, methyl methacrylate and N-vinylpyrrolidone in amounts of 55%, 35% and 10% by weight, respectively, was prepared as follows:

To a 2-liter split resin flask fitted with a condenser, stirrer, temperature control and nitrogen purge was added 330 g of isooctyl acrylate, 210 g of methyl methacrylate, 60 g of N-vinylpyrrolidone, 3 g of α,α'-azobisisobutyronitrile and 600 g of acetone. The flask was then heated to 55° C. accompanied by nitrogen purge and agitation at about 250 rpm. After 22 hours, 400 g of acetone was added to the mixture, and agitation was continued until the mixture was uniform. The resulting mixture contained 42.7% solids, has a Brookfield viscosity of 1800 cp and an inherent viscosity of 0.61 dl/g in ethyl acetate at 0.15 g/dl. No unreacted monomer was detected by gas chromatography.

A film cast from the above copolymer preparation exhibited a tensile strength of 1187 psi and an elongation of 285% when tested in accordance with Test Method D.

Twenty g of iodine crystals and 24 g of sodium iodide were dissolved in 56 g of anhydrous ethanol. This solution was used to incorporate iodine into the film-forming copolymer as follows:

To 100 g of the 42.7% solids solution of the film-forming copolymer prepared above was added 11.2 g of the above iodine-iodide solution and 333.9 g of ethanol to provide a film-forming composition containing 0.5% iodine based upon the total weight of the film-forming copolymer, iodine, iodide and solvent.

When the above composition was applied to skin, it dried in less than 5 minutes under the conditions of Test Method A to provide a clear film which was substantially tack-free when tested in accordance with Test Method A. The film adhered suitably to skin as determined in accordance with Test Method C.

The composition provided a film which was substantially fluid-resistant. Further, when the composition was tested in accordance with Test Method B, the film remained intact through an average of 59 scrubs.

A film which is solvent-cast onto a release paper in a thickness of 1.8 mil (when dry) would have a suitable moisture vapor transmission rate.

A 0.7 mil thick (0.0018 centimeter-thick) antimicrobial film obtained using the composition of this Example and a control film containing no iodine were cut into one-inch squares (2.54 cm squares). The squares of film were placed in the bottom of a moist chamber and coated with 0.05 ml of a saline suspension of *S. aureus*. At intervals of 30, 45 and 90 minutes, the films were removed, placed in blenders containing 0.1% sodium thiosulfate to neutralize residual iodine, and macerated for 5 minutes. An aliquot of each homogenate was serially diluted and the dilutions were plated in nutrient agar comprising 10 cc of the *M-enterococcus* media "Difco Media 6785" (commercially available from Difco Laboratory). Plate colony counts were made after incubation at 37° C. for 48 hours. The log 10 reduction in organism colony numbers was determined by calculating the numerical difference between colony counts from the antimicrobial film test plates and colony counts from the control film test plates. When tested in the above manner the antimicrobial film exhibited greater than a 4-log reduction in colony numbers of *S. aureus* at 30, 45 and 90 minutes.

The composition was dermatologically-acceptable to skin as determined by a method modified slightly from that described in J. H. Draize et al, *J. Pharmacol. Exp. Ther.*, 82, 377 (1944), incorporated herein by reference. More particularly, the composition gave a test score of 0.3, the control value being 0.0 and a score of less than 2.0 being acceptable.

EXAMPLES 2-8

Additional film-forming compositions of the invention were prepared as follows:

Film-forming copolymers A-G were prepared using the monomer types and amounts (expressed in grams) shown in Table I below:

TABLE I

| Monomer | Film-Forming Copolymer | | | | | | |
|---|---|---|---|---|---|---|---|
| | A | B | C | D | E | F | G |
| n-Butyl acrylate | 110 | 120 | | | | | |
| Isooctyl acrylate | | | 120 | 100 | 90 | | 50 |
| Methyl methacrylate | 70 | 60 | 60 | 80 | 90 | 70 | |
| n-Butyl methacrylate | | | | | | | 130 |
| Lauryl methacrylate | | | | | | 110 | |

TABLE I-continued

| Monomer | Film-Forming Copolymer | | | | | | |
|---|---|---|---|---|---|---|---|
| | A | B | C | D | E | F | G |
| N—Vinylpyrrolidone | 20 | 20 | 20 | 20 | 20 | 20 | 20 |

The film-forming copolymers A–G indicated were prepared as follows:

For each copolymer, the respective monomers in the respective amounts were added to a quart brown glass bottle having a narrow neck. One g of α,α'-azobisisobutyronitrile and 200 g of either acetone (copolymers A, B, E, F, and G) or ethyl acetate (copolymers C and D) are also added to the bottle. The bottle was purged to eliminate air therefrom by passing nitrogen through the air space above the solution at a rate of 1 liter per minute. The bottle was then sealed, and was tumbled for 24 hours in a water both maintained at 55° C. Copolymers C and D were then further diluted wth 200 g of ethyl acetate due to a relatively high viscosity of the polymer mixture. The copolymer preparations obtained above had the following solids content: 49.5% for A; 49.4% for B; 32.1% for C; 32.4% for D; 49.9% for E; 47.1% for F; and 49.3% for G.

Films obtained from the above copolymer preparations exhibited tensile strength and elongation values as follows when tested in accordance with Test Method D:

Copolymer A, 1610 psi and 369%;
Copolymer B, 840 psi and 554%;
Copolymer C, 1163 psi and 312%;
Copolymer D, 1165 psi and 210%;
Copolymer E, 2089 psi and 176%;
Copolymer F, 716 psi and 218%; and
Copolymer G, 914 psi and 433%.

The above copolymer solutions were combined with the iodine/iodide solution of Example 1 and ethanol and/or acetone in the amounts indicated in Table II below to provide film-forming compositions containing 0.5% iodine by weight.

TABLE II

| Example | Copolymer solution (and amount in g) | Iodine/Iodide Solution (g) | Solvents (and amount(s) in g) |
|---|---|---|---|
| 2 | A (50) | 6.45 | Ethanol (201.4) |
| 3 | B (50) | 6.45 | Ethanol (201.0) |
| 4 | C (100) | 8.8 | Ethanol (245) |
| 5 | D (100) | 8.8 | Ethanol (245) |
| 6 | E (50) | 6.5 | Ethanol (153.3) and Acetone (50) |
| 7 | F (50) | 6.2 | Acetone (184.9) |
| 8 | G (50) | 6.45 | Ethanol (200.5) |

All of the above compositions dried in less than 5 minutes under the conditions of Test Method A to provide clear films which were substantially tack-free when tested in accordance with Test Method A, and adhered suitably to skin when tested in accordance with Test Method C.

The above compositions provided films which were substantially fluid-resistant. Further, when the composition of Example 6 was tested in accordance with Test Method B, the resulting film remained intact through an average of 33 scrubs. Also, the compositions of Examples 2–5 and 7–8, if tested in accordance with Test Method B, would similarly provide films which would remain intact through at least 20 scrubs.

A film which was 1.8 mil in thickness (when dry) and provided by the film-forming composition of Example 4 exhibited a moisture vapor transmission rate of 600 g/meter$^2$/24 hours when measured at 40° C. using a 80% relative humidity differential across the film.

EXAMPLE 9

A film-forming composition of the invention was prepared as follows:

A film-forming copolymer containing isooctyl acrylate, methyl methacrylate and N-vinylpyrrolidone in amounts of 55%, 35% and 10% by weight, respectively, was prepared in accordance with the procedure of Examples 2–8 using acetone as the solvent. The resulting copolymer preparation was 49.8% solids by weight.

Twenty-five g of the above copolymer preparation was combined with 0.79 g of chlorhexidine acetate, 50 g of ethanol and 48 g of acetone. A crystal clear solution was obtained indicating the absence of any chemical incompatibility. It is believed that the composition would provide a clear, substantially fluid-resistant, substantially tack-free, flexible film which adheres to skin and releases the antimicrobial agent to skin.

COMPARATIVE EXAMPLES 10–15

Compositions were prepared as follows:

Copolymers H–M were prepared following the procedure of Examples 2–8 using the monomer types and amounts (again expressed in grams) shown in Table III below:

TABLE III

| Monomer | Copolymer | | | | | |
|---|---|---|---|---|---|---|
| | H | I | J | K | L | M |
| Methyl acrylate | 160 | | | | | |
| Isooctyl acrylate | | | 140 | 160 | 100 | 70 |
| Methyl methacrylate | 20 | | 40 | 20 | | |
| n-Butyl methacrylate | | 90 | | | | 110 |
| N—Vinylpyrrolidone | 20 | 20 | 20 | 20 | 20 | 20 |
| Stearyl methacrylate | | | | | 80 | |
| Lauryl methacrylate | | 90 | | | | |

The copolymer preparations obtained above had the following solids content: 32.5% for H; 47.8% for I; 31.7% for J; 31.3% for K; 48.4% for L; and 49.0% for M.

Films obtained from the above copolymer preparations H, I and M exhibited tensile strengths and elongation values as follows when tested in accordance with Test Method C:

Copolymer H, 3101 psi, 0%;
Copolymer I, 2497 psi, 23%; and
Copolymer M, 248 psi, 657%.

Tensile strengths and elongation values were not determined on copolymer J, K or L since these copolymers were very tacky to the touch.

The above H, I, J, K and M copolymer solutions were combined with the iodine/iodide solution of Example 1 and ethanol or acetone in the amounts indicated in Table IV below to provide compositions containing 0.5% iodine by weight (again, copolymer L was very tacky and therefore was not tested further (Comparative Example 14)).

TABLE IV

| Comparative Example | Copolymer solution (and amount in g) | Iodine/Iodide Solution (g) | Solvent (and amount in g) |
|---|---|---|---|
| 10 | H (50) | 4.3 | Acetone (115.3) |
| 11 | I (50) | 6.3 | Acetone (193) |
| 12 | J (100) | 8.8 | Ethanol (245) |

TABLE IV-continued

| Comparative Example | Copolymer solution (and amount in g) | Iodine/Iodide Solution (g) | Solvent (and amount in g) |
|---|---|---|---|
| 13 | K (100) | 8.8 | Ethanol (245) |
| 15 | M (50) | 6.4 | Ethanol (198.9) |

When the compositions of Comparative Examples 10–13 and 15 were evaluated, the following was observed.

The compositions of Comparative Examples 10 and 11 provided substantially tack-free films when tested in accordance with Test Method A. Further, both films were suitable fluid-resistant and adhered suitably to skin. However, films obtained from compositions comprising the respective copolymers, but not iodine, were brittle (i.e., inflexible) as evidenced by relatively high tensile strengths and low elongation values as determined by Test Method D as discussed above.

The compositions of Comparative Examples 12, 13 and 15 provided films which were suitably fluid-resistant and adhered suitably to skin. However, all three compositions failed to provide films which were suitably tack-free when tested in accordance with Test Method A.

What is claimed is:

1. A film-forming composition, comprising:
(a) a film-forming copolymer consisting essentially of copolymerized A, B and C monomers as follows:
  A is a monomeric acrylic or methacrylic acid ester of an alkyl alcohol containing a single hydroxyl, said alcohol having from 2 to about 14 carbon atoms when said A monomer is an acrylic acid ester, and 7 to 18 carbon atoms when said A monomer is a methacrylic acid ester, the amount by weight of A monomer being about 15 to 80% of the total weight of all monomers in the copolymer;
  B is a monomeric methacrylic acid ester of an alkyl alcohol containing a single hydroxyl, said alcohol having from 1 to 6 carbon atoms, the amount by weight of B monomer being about 20 to 70% of the total weight of all monomers in the copolymer; and
  C is an N-vinyl lactam, the amount by weight of which being about 1 to 15% of the total weight of all monomers in the copolymer;
(b) an effective amount of a broad spectrum antimicrobial agent;
said composition being dermatologically-acceptable, and, when applied to skin from a fugitive solvent, being capable of forming a clear, substantially fluid-resistant, substantially tack-free, flexible film which adheres to skin and releases said antimicrobial agent to skin.

2. A film-forming composition according to claim 1, wherein said antimicrobial agent is iodine which forms a complex with said film-forming copolymer via the N-vinyl lactam residues contained therein, the amount by weight of iodine being about 0.1 to 15% of the total weight of said film-forming copolymer and said iodine.

3. A film-forming composition according to claim 2, wherein said alcohol of said A monomer contains about 4–14 carbon atoms when said A monomer is an acrylic acid ester, and about 10–18 carbon atoms when said A monomer is a methacrylic acid ester.

4. A film-forming composition according to claim 2, wherein said alcohol of said B monomer contains 1 to about 4 carbon atoms.

5. A film-forming composition according to claim 2, wherein said C monomer is N-vinylpyrrolidone.

6. A film-forming composition according to claim 2, wherein said A monomer is selected from the group consisting of n-butyl acrylate, isooctyl acrylate and lauryl methacrylate.

7. A film-forming composition according to claim 2, wherein said A monomer is isooctyl acrylate.

8. A film-forming composition according to claim 2, wherein said B monomer is selected from the group consisting of methyl methacrylate and n-butyl methacrylate.

9. A film-forming composition according to claim 2, wherein said B monomer is methyl methacrylate.

10. A film-forming composition according to claim 2, wherein the amount by weight of said A monomer is about 40 to 60% of the total weight of all monomers in said copolymer.

11. A film-forming composition according to claim 2, wherein the amount by weight of said B monomer is about 25 to 50% of the total weight of all monomers in said copolymer.

12. A film-forming composition according to claim 2, wherein said C monomer is present in an amount by weight of about 5–15% of the total weight of all monomers in said copolymer.

13. A film-forming composition according to claim 2, wherein said iodine is present in an amount by weight of about 2–12% of the total weight of said film-forming copolymer and said iodine.

14. A film-forming composition according to claim 13, wherein said alcohol of said A monomer contains about 4–14 carbon atoms when said A monomer is an acrylic acid ester, and about 10–18 carbon atoms when said A monomer is a methacrylic acid ester; said alcohol of said B monomer contains 1 to about 4 carbon atoms; and said C monomer is N-vinylpyrrolidone.

15. A film-forming composition according to claim 14, wherein said C monomer is present in an amount by weight of about 5–15% of the total weight of all monomers in said copolymer, and said iodine is present in an amount by weight of about 2–12% of the total weight of said film-forming copolymer and said iodine.

16. A film-forming composition according to claim 15, wherein said A monomer is selected from the group consisting of n-butyl acrylate, isooctyl acrylate and lauryl methacrylate, and said B monomer is selected from the group consisting of methyl methacrylate and n-butyl methacrylate.

17. A film-forming composition according to claim 15, wherein said A monomer is isooctyl acrylate and said B monomer is methyl methacrylate.

18. A film-forming composition according to claim 2, further comprising an alcohol selected from the group consisting of ethanol and isopropanol, said film-forming polymer being dissolved in said alcohol, and said alcohol being present in an amount of about 20 to 1000 parts by weight per 10 parts by weight of the total of said film-forming copolymer and said iodine.

19. A film-forming composition according to claim 2, further comprising an inorganic iodide which functions to increase the stability of the complex of iodine with said film-forming copolymer.

20. A film-forming composition according to claim 1, wherein said antimicrobial agent is chlorhexidine or a derivative thereof.

21. A method of promoting asepsis on mammalian skin, comprising the steps of: (a) applying to said skin said composition of claim 1; (b) allowing said composition to dry to form said film, and (c) allowing said film to remain on said skin to promote said asepsis.

22. A method according to claim 21, wherein said film is subsequently removed using a solvent.

23. A method according to claim 21, wherein said film is covered during a surgical procedure with a surgical drape comprising a pressure-sensitive adhesive layer which is contacted with said film.

24. A method according to claim 23, wherein said film is subsequently removed by removing said surgical drape.

25. A method according to claim 21, wherein said antimicrobial agent is iodine.

26. A method according to claim 21, wherein said antimicrobial agent is chlorhexidine or a derivative thereof.

* * * * *